(12) United States Patent
Pastan et al.

(10) Patent No.: US 7,375,183 B1
(45) Date of Patent: May 20, 2008

(54) MESOTHELIN, IMMUNOGENIC PEPTIDES DERIVED THEREFROM, AND COMPOSITIONS COMPRISING MESOTHELIN, OR IMMUNOGENIC PEPTIDES THEREOF

(75) Inventors: Ira Pastan, Potomac, MD (US); Kai Chang, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 189 days.

(21) Appl. No.: 09/684,599

(22) Filed: Oct. 5, 2000

Related U.S. Application Data

(62) Division of application No. 09/215,035, filed on Dec. 17, 1998, now Pat. No. 6,153,430, which is a division of application No. 08/776,271, filed as application No. PCT/US97/00224 on Jan. 3, 1997, now Pat. No. 6,083,502.

(60) Provisional application No. 60/010,166, filed on Jan. 5, 1996.

(51) Int. Cl.
*C07K 1/00* (2006.01)
*C07K 17/02* (2006.01)

(52) U.S. Cl. .................. 530/350; 530/402; 530/403
(58) Field of Classification Search ............. 424/184.1, 424/185.1, 277.1, 186.1; 530/350
See application file for complete search history.

(56) References Cited

U.S. PATENT DOCUMENTS

| | | | |
|---|---|---|---|
| 5,320,956 A | 6/1994 | Willingham et al. | 435/172.2 |
| 5,498,698 A | 3/1996 | Yamaguchi et al. | 530/399 |
| 5,608,039 A | 3/1997 | Pastan et al. | 530/387.3 |
| 5,723,318 A | 3/1998 | Yamaguchi et al. | 435/69.5 |

FOREIGN PATENT DOCUMENTS

| | | |
|---|---|---|
| WO | WO 89/01629 | 2/1989 |
| WO | WO 92/07081 | 4/1992 |
| WO | WO 94/10312 | 5/1994 |

OTHER PUBLICATIONS

Ezzel, The Journal of NIH Research, vol. 7, pp. 46-49, Jan. 1995.*
Spitler, Cancer Biotherapy, vol. 10, No. 1, pp. 1-3, 1995.*
Evans et al., QJM, Journal of the Association of Physicians, vol. 92, No. 6, pp. 299-307, Jun. 1999.*
Bowie et al (Science, 1990, 257:1306-1310).*
Burgess et al (J. Cell Bio., 1990, 111:2129-2138).*
Lazar et al (Mol. Cell. Biol., 1988, 8:1247-1252).*
Scott et al (Nature Genetics, 1999, 21:440-443).*
Bork (Genome Research, 2000, 10:398-400).*
Roitt et al (1998, Immunology, 4th Ed., Mosb, Londonp 7.7-7.8.*
Holmes (Exp. Opin. Invest. Drugs, 2001, 10(3):511-519).*
Herbert et al (The Dictionary of Immunology, Academic Press, 4th edition, 1995, p. 58).*
Kirkin et al, 1998, APMIS, 106:665-679).*
Chaux et al, Int J. Cancer, 1998, 77:538-542).*
Sherman et al, 1998, Crit. Rev in Innumol., 18(1-2):47-54).*
Smith, Clin. Immunol., 41(4):841-849).*
Boon (Adv Can Res., 1992, 58:177-2100.*
Taber's Cyclopedic Medical Dictionary, FA Davis, Philadelphia, 16th Ed., 1985, p. 1354.*
Herbert et al (The Dictionary of Immunology, Academic Press, 3rd Edition, London, 1985, pp. 58-59.*
Yamaguchi, Nozomi et al., "A Novel Cytokine Exhibiting Megakaryocyte Potentiating Activity From a Human Pancreatic Tumor Cell Line HPC-Y5", *J. Biol. Chem.* vol. 269, No. 2: 805-808 (1994).
Chang, K. et al., *Intl. J. Cancer.*, 50:373 (1992).
Chang, K. et al., *Intl. J. Cancer*, 57:90 (1994).
Chang, K. et al., *Intl. J. Cancer*, 51:548 (1992).
Tetsu Kojima et al., *Journal of Biological Chemistry*, 270:21984 (1995).
Chang, K. et al., *Proceedings of the National Academy of Sciences of the United States of America*, 93:136 (1996).
Bast, R. et al., *N. Eng. J. Med.*, 309:883-887 (1983).
Campbell, I.G. et al., *Cancer Res.*, 51:5329-5338 (1991).
Chang, K. et al., *Am. J. Surg. Pathol.*, 16:259-268 (1992).
Akiyama, Shin-Ichi et al., *J. of Cell. Phys.*, 120:271-279 (1984).
Database Geneseq. Accession No. R53991. Hattori, K. et al. Megakaryocyte potentiator. (1994).

* cited by examiner

*Primary Examiner*—Susan Ungar
(74) *Attorney, Agent, or Firm*—Townsend and Townsend and Crew LLP

(57) ABSTRACT

This invention relates to the discovery of a differentiation antigen termed mesothelin which is associated with mesotheliomas and ovarian cancers. Mesothelin is about 69 kD in its full-length form. The invention includes uses for the amino acid and nucleic acid sequences for mesothelin, recombinant cells expressing it, methods for targeting and/or inhibiting the growth of cells bearing mesothelin, methods for detecting the antigen and its expression level as an indication of the presence of tumor cells, and kits for such detection.

3 Claims, 3 Drawing Sheets

FIG. 1-1.

```
1121  CCTTCACCTACGAGAGCACCTGGAGCGTCCTAAAGCATAAACTGGATGAGCTCTACCCCAGTCTGTGATC
342      F  T  Y  E  Q  L  D  V  L  K  H  K  L  D  E  L  T  P  Q  G  Y  P  E  S  V  I
1201  CAGCACCTGGGCTACCTCTTCCTCAAGATCAGCCCTGAGGACATTCGCAAGTGGAATGTGACCCTCCTCGAGACCCTGAA
368      Q  M  L  G  T  L  F  L  K  M  S  P  E  D  I  E  K  W  N  V  T  E  L  R  T  L  K
1281  GGCTTTGCTTGAAGTCGACAAAGCCACGAAATCACTCCTCAGCCTCCTCGGCGCCCCACAGGTCGCCACCCTGA
395      A  L  L  E  V  D  K  G  M  E  M  S  P  Q  A  P  R  R  P  L  P  Q  V  A  T  L  I
1361  TCGACCGCTTTGTGAAGGGAAGGGGCCAGCTAGACAAAGACACCCTAGACACCCTGACCAAGCCCTACCCTGGGTACCTG
422      D  R  F  V  K  G  R  G  Q  L  D  K  D  T  L  D  T  L  T  K  P  Y  P  G  Y  L
1441  TGCTCCCTCAGCCCTGAGGAGCTGAGCTCCGTGCCCCCATCTGGGCGGTCAGGCCCCAGGACCTGGACACGTG
448      C  S  L  S  P  E  E  L  S  S  V  P  P  S  S  I  W  A  V  R  P  Q  D  L  D  T  C
1521  TGACCCAAGGCAGCTGGACCTCCTCTATCCCAAGGCCCGTCTTTCCAGAACATGAACCGTCCGAATACTTCGTGA
475      D  F  Q  L  D  V  L  Y  P  K  A  R  L  A  F  Q  N  M  K  G  S  E  Y  P  V  K
1601  AGATCAGTCCTTCCTGGGTGGGGCCCCACGGAGATTGAAGCCGCTCAGTCAGCAGAATGTGAGCATGGACTTCGCC
502      I  Q  S  P  L  G  G  A  P  T  E  D  L  K  A  L  S  Q  Q  N  V  S  M  D  L  A
1681  ACGTTCATGAAGCTGCGCGACGGATCCGGTCCTGCCGTTGACTGTGGCTGAGGTGCAGAAACTTCTGGGACCCCACGTGGA
528      T  F  M  K  L  R  T  D  A  V  L  P  L  T  V  A  E  V  Q  K  L  L  C  D  M  V  E
1761  GGGCCTGAAGGCCGAAGAGGAGCGGCATCGACCTCTACGGCCAGGACGACCTGGACACGCTGG
555      G  L  K  A  E  E  R  H  R  P  V  R  D  W  I  L  R  Q  D  D  L  D  T  L  G
1841  GGCTGGGGCTACAGGGCGGCATCGAGAACTGCTACCTGGTCCTGGACCTGCAAGACACCCTCTCGGGGACGCCC
582      L  G  L  Q  G  G  I  E  N  C  Y  L  V  L  D  L  S  V  Q  E  T  L  S  C  T  P
1921  TGCCTCCTCTGCCCCCCAGCCCTCCTCGGGATCCCGCCTGCCCACCACCAGCCAGCCGGGTGATCCCGTTCCACCCCAAGAGAACTC
610      C  L  L  C  P  G  P  V  L  T  V  L  A  L  L  A  S  T  L  A
2001  TCCTCCCCCCAGCCCTCCTCGGGATCCCGCCTGCCCACCACCAGCCAGCCGGGTGATCCCGTTCCACCCCAAGAGAACTC
2081  GCCCTCAGTAAACGGGAACATGCCCCCTGCAGAACAAAAAAAAAAAAAAAAAAAAAA  2138
```

FIG. 1-2.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH: 2138 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 100..1986

(xi) SEQUENCE DESCRIPTION: SEQ ID NO: 1:

```
AGGAATTCCG GTGGCCGGCC ACTCCCGTCT GCTGTGACGC GCGGACAGAG AGCTACCGGT        60

GGACCCACGG TGCCTCCCTC CCTGGGATCT ACACAGACC ATG GCC TTG CAA CGG         114
                                            Met Ala Leu Gln Arg
                                              1               5

CTC GAC CCC TGT TGG TCC TGT GGG GAC CGC CCT GGC AGC CTC CTG TTC        162
Leu Asp Pro Cys Trp Ser Cys Gly Asp Arg Pro Gly Ser Leu Leu Phe
             10                  15                  20

CTG CTC TTC AGC CTC GGA TGG GTG CAT CCC GCG AGG ACC CTG GCT GGA        210
Leu Leu Phe Ser Leu Gly Trp Val His Pro Ala Arg Thr Leu Ala Gly
         25                  30                  35

GAG ACA GGG ACG GAG TCT GCC CCC CTG GGG GGA GTC CTG ACA ACC CCC        258
Glu Thr Gly Thr Glu Ser Ala Pro Leu Gly Gly Val Leu Thr Thr Pro
     40                  45                  50

CAT AAC ATT TCC AGC CTC TCC CCT CGC CAA CTC CTT GGC TTC CCG TGT        306
His Asn Ile Ser Ser Leu Ser Pro Arg Gln Leu Leu Gly Phe Pro Cys
 55                  60                  65

GCG GAG GTG TCC GGC CTG AGC ACG GAG CGT GTC CGG GAG CTG GCT GTG        354
Ala Glu Val Ser Gly Leu Ser Thr Glu Arg Val Arg Glu Leu Ala Val
 70                  75                  80                  85

GCC TTG GCA CAG AAG AAT GTC AAG CTC TCA ACA GAG CAG CTG CGC TGT        402
Ala Leu Ala Gln Lys Asn Val Lys Leu Ser Thr Glu Gln Leu Arg Cys
                 90                  95                 100

CTG GCT CAC CGG CTC TCT GAG CCC CCC GAG GAC CTG GAC GCC CTC CCA        450
Leu Ala His Arg Leu Ser Glu Pro Pro Glu Asp Leu Asp Ala Leu Pro
                 105                 110                 115

TTG GAC CTG CTG CTA TTC CTC AAC CCA GAT GCG TTC TCG GGG CCC CAG        498
Leu Asp Leu Leu Leu Phe Leu Asn Pro Asp Ala Phe Ser Gly Pro Gln
             120                 125                 130

GCC TGC ACC CGT TTC TTC TCC CGC ATC ACG AAG GCC AAT GTG GAC CTG        546
Ala Cys Thr Arg Phe Phe Ser Arg Ile Thr Lys Ala Asn Val Asp Leu
         135                 140                 145

CTC CCG AGG GGG GCT CCC GAG CGA CAG CGG CTG CTG CCT GCG GCT CTG        594
Leu Pro Arg Gly Ala Pro Glu Arg Gln Arg Leu Leu Pro Ala Ala Leu
150                 155                 160                 165

GCC TGC TGG GGT GTG CGG GGG TCT CTG CTG AGC GAG GCT GAT GTG CGG        642
Ala Cys Trp Gly Val Arg Gly Ser Leu Leu Ser Glu Ala Asp Val Arg
                 170                 175                 180

GCT CTG GGA GGC CTG GCT TGC GAC CTG CCT GGG CGC TTT GTG GCC GAG        690
Ala Leu Gly Gly Leu Ala Cys Asp Leu Pro Gly Arg Phe Val Ala Glu
             185                 190                 195

TCG GCC GAA GTG CTG CTA CCC CGG CTG GTG AGC TGC CCG GGA CCC CTG        738
```

```
                -continued

Ser Ala Glu Val Leu Leu Pro Arg Leu Val Ser Cys Pro Gly Pro Leu
        200                 205                 210

GAC CAG GAC CAG CAG GAG GCA GCC AGG GCG GCT CTG CAG GGC GGG GGA         786
Asp Gln Asp Gln Gln Glu Ala Ala Arg Ala Ala Leu Gln Gly Gly Gly
        215                 220                 225

CCC CCC TAC GGC CCC CCG TCG ACA TGG TCT GTC TCC ACG ATG GAC GCT         834
Pro Pro Tyr Gly Pro Pro Ser Thr Trp Ser Val Ser Thr Met Asp Ala
230                 235                 240                 245

CTG CGG GGC CTG CTG CCC GTG CTG GGC CAG CCC ATC ATC CGC AGC ATC         882
Leu Arg Gly Leu Leu Pro Val Leu Gly Gln Pro Ile Ile Arg Ser Ile
                250                 255                 260

CCG CAG GGC ATC GTG GCC GCG TGG CGG CAA CGC TCC TCT CGG GAC CCA         930
Pro Gln Gly Ile Val Ala Ala Trp Arg Gln Arg Ser Ser Arg Asp Pro
        265                 270                 275

TCC TGG CGG CAG CCT GAA CGG ACC ATC CTC CGG CCG CGG TTC CGG CGG         978
Ser Trp Arg Gln Pro Glu Arg Thr Ile Leu Arg Pro Arg Phe Arg Arg
        280                 285                 290

GAA GTG GAG AAG ACA GCC TGT CCT TCA GGC AAG AAG GCC CGC GAG ATA        1026
Glu Val Glu Lys Thr Ala Cys Pro Ser Gly Lys Lys Ala Arg Glu Ile
        295                 300                 305

GAC GAG AGC CTC ATC TTC TAC AAG AAG TGG GAG CTG GAA GCC TGC GTG        1074
Asp Glu Ser Leu Ile Phe Tyr Lys Lys Trp Glu Leu Glu Ala Cys Val
310                 315                 320                 325

GAT GCG GCC CTG CTG GCC ACC CAG ATG GAC CGC GTG AAC GCC ATC CCC        1122
Asp Ala Ala Leu Leu Ala Thr Gln Met Asp Arg Val Asn Ala Ile Pro
                330                 335                 340

TTC ACC TAC GAG CAG CTG GAC GTC CTA AAG CAT AAA CTG GAT GAG CTC        1170
Phe Thr Tyr Glu Gln Leu Asp Val Leu Lys His Lys Leu Asp Glu Leu
        345                 350                 355

TAC CCA CAA GGT TAC CCC GAG TCT GTG ATC CAG CAC CTG GGC TAC CTC        1218
Tyr Pro Gln Gly Tyr Pro Glu Ser Val Ile Gln His Leu Gly Tyr Leu
        360                 365                 370

TTC CTC AAG ATG AGC CCT GAG GAC ATT CGC AAG TGG AAT GTG ACG TCC        1266
Phe Leu Lys Met Ser Pro Glu Asp Ile Arg Lys Trp Asn Val Thr Ser
        375                 380                 385

CTG GAG ACC CTG AAG GCT TTG CTT GAA GTC GAC AAA GGG CAC GAA ATG        1314
Leu Glu Thr Leu Lys Ala Leu Leu Glu Val Asp Lys Gly His Glu Met
390                 395                 400                 405

AGT CCT CAG GCT CCT CGG CGG CCC CTC CCA CAG GTG GCC ACC CTG ATC        1362
Ser Pro Gln Ala Pro Arg Arg Pro Leu Pro Gln Val Ala Thr Leu Ile
                410                 415                 420

GAC CGC TTT GTG AAG GGA AGG GGC CAG CTA GAC AAA GAC ACC CTA GAC        1410
Asp Arg Phe Val Lys Gly Arg Gly Gln Leu Asp Lys Asp Thr Leu Asp
        425                 430                 435

ACC CTG ACC GCC TTC TAC CCT GGG TAC CTG TGC TCC CTC AGC CCC GAG        1458
Thr Leu Thr Ala Phe Tyr Pro Gly Tyr Leu Cys Ser Leu Ser Pro Glu
        440                 445                 450

GAG CTG AGC TCC GTG CCC CCC AGC AGC ATC TGG GCG GTC AGG CCC CAG        1506
Glu Leu Ser Ser Val Pro Pro Ser Ser Ile Trp Ala Val Arg Pro Gln
        455                 460                 465

GAC CTG GAC ACG TGT GAC CCA AGG CAG CTG GAC GTC CTC TAT CCC AAG        1554
Asp Leu Asp Thr Cys Asp Pro Arg Gln Leu Asp Val Leu Tyr Pro Lys
470                 475                 480                 485

GCC CGC CTT GCT TTC CAG AAC ATG AAC GGG TCC GAA TAC TTC GTG AAG        1602
Ala Arg Leu Ala Phe Gln Asn Met Asn Gly Ser Glu Tyr Phe Val Lys
                490                 495                 500

ATC CAG TCC TTC CTG GGT GGG GCC CCC ACG GAG GAT TTG AAG GCG CTC        1650
Ile Gln Ser Phe Leu Gly Gly Ala Pro Thr Glu Asp Leu Lys Ala Leu
        505                 510                 515
```

-continued

```
AGT CAG CAG AAT GTG AGC ATG GAC TTG GCC ACG TTC ATG AAG CTG CGG    1698
Ser Gln Gln Asn Val Ser Met Asp Leu Ala Thr Phe Met Lys Leu Arg
    520                 525                 530

ACG GAT GCG GTG CTG CCG TTG ACT GTG GCT GAG GTG CAG AAA CTT CTG    1746
Thr Asp Ala Val Leu Pro Leu Thr Val Ala Glu Val Gln Lys Leu Leu
535                 540                 545

GGA CCC CAC GTG GAG GGC CTG AAG GCG GAG GAG CGG CAC CGC CCG GTG    1794
Gly Pro His Val Glu Gly Leu Lys Ala Glu Glu Arg His Arg Pro Val
550                 555                 560                 565

CGG GAC TGG ATC CTA CGG CAG CGG CAG GAC GAC CTG GAC ACG CTG GGG    1842
Arg Asp Trp Ile Leu Arg Gln Arg Gln Asp Asp Leu Asp Thr Leu Gly
            570                 575                 580

CTG GGG CTA CAG GGC GGC ATC CCC AAC GGC TAC CTG GTC CTA GAC CTC    1890
Leu Gly Leu Gln Gly Gly Ile Pro Asn Gly Tyr Leu Val Leu Asp Leu
            585                 590                 595

AGC GTG CAA GAG ACC CTC TCG GGG ACG CCC TGC CTC CTA GGA CCT GGA    1938
Ser Val Gln Glu Thr Leu Ser Gly Thr Pro Cys Leu Leu Gly Pro Gly
            600                 605                 610

CCT GTT CTC ACC GTC CTG GCA CTG CTC CTA GCC TCC ACC CTG GCC        1983
Pro Val Leu Thr Val Leu Ala Leu Leu Leu Ala Ser Thr Leu Ala
615                 620                 625

TGAGGGCCCC ACTCCCTTGC TGGCCCCAGC CCTGCTGGGG ATCCCCGCCT GGCCAGGAGC  2043

AGGCACGGGT GATCCCCGTT CCACCCCAAG AGAACTCGCG CTCAGTAAAC GGGAACATGC  2103

CCCCTGCAGA CAAAAAAAAA AAAAAAAAA AAAA                               2138

(2) INFORMATION FOR SEQ ID NO: 2:

(i) SEQUENCE CHARACTERISTICS:
        (A) LENGTH: 628 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Leu Gln Arg Leu Asp Pro Cys Trp Ser Cys Gly Asp Arg Pro
1               5                   10                  15

Gly Ser Leu Leu Phe Leu Leu Phe Ser Leu Gly Trp Val His Pro Ala
            20                  25                  30

Arg Thr Leu Ala Gly Glu Thr Gly Thr Glu Ser Ala Pro Leu Gly Gly
        35                  40                  45

Val Leu Thr Thr Pro His Asn Ile Ser Ser Leu Ser Pro Arg Gln Leu
    50                  55                  60

Leu Gly Phe Pro Cys Ala Glu Val Ser Gly Leu Ser Thr Glu Arg Val
65                  70                  75                  80

Arg Glu Leu Ala Val Ala Leu Ala Gln Lys Asn Val Lys Leu Ser Thr
                85                  90                  95

Glu Gln Leu Arg Cys Leu Ala His Arg Leu Ser Glu Pro Pro Glu Asp
            100                 105                 110

Leu Asp Ala Leu Pro Leu Asp Leu Leu Leu Phe Leu Asn Pro Asp Ala
        115                 120                 125

Phe Ser Gly Pro Gln Ala Cys Thr Arg Phe Phe Ser Arg Ile Thr Lys
    130                 135                 140

Ala Asn Val Asp Leu Leu Pro Arg Gly Ala Pro Glu Arg Gln Arg Leu
145                 150                 155                 160

Leu Pro Ala Ala Leu Ala Cys Trp Gly Val Arg Gly Ser Leu Leu Ser
                165                 170                 175
```

```
Glu Ala Asp Val Arg Ala Leu Gly Gly Leu Ala Cys Asp Leu Pro Gly
            180                 185                 190

Arg Phe Val Ala Glu Ser Ala Glu Val Leu Leu Pro Arg Leu Val Ser
        195                 200                 205

Cys Pro Gly Pro Leu Asp Gln Asp Gln Gln Glu Ala Ala Arg Ala Ala
    210                 215                 220

Leu Gln Gly Gly Gly Pro Pro Tyr Gly Pro Ser Thr Trp Ser Val
225                 230                 235                 240

Ser Thr Met Asp Ala Leu Arg Gly Leu Leu Pro Val Leu Gly Gln Pro
                245                 250                 255

Ile Ile Arg Ser Ile Pro Gln Gly Ile Val Ala Ala Trp Arg Gln Arg
            260                 265                 270

Ser Ser Arg Asp Pro Ser Trp Arg Gln Pro Glu Arg Thr Ile Leu Arg
        275                 280                 285

Pro Arg Phe Arg Arg Glu Val Glu Lys Thr Ala Cys Pro Ser Gly Lys
    290                 295                 300

Lys Ala Arg Glu Ile Asp Glu Ser Leu Ile Phe Tyr Lys Lys Trp Glu
305                 310                 315                 320

Leu Glu Ala Cys Val Asp Ala Ala Leu Leu Ala Thr Gln Met Asp Arg
                325                 330                 335

Val Asn Ala Ile Pro Phe Thr Tyr Glu Gln Leu Asp Val Leu Lys His
            340                 345                 350

Lys Leu Asp Glu Leu Tyr Pro Gln Gly Tyr Pro Glu Ser Val Ile Gln
        355                 360                 365

His Leu Gly Tyr Leu Phe Leu Lys Met Ser Pro Glu Asp Ile Arg Lys
    370                 375                 380

Trp Asn Val Thr Ser Leu Glu Thr Leu Lys Ala Leu Leu Glu Val Asp
385                 390                 395                 400

Lys Gly His Glu Met Ser Pro Gln Ala Pro Arg Arg Pro Leu Pro Gln
                405                 410                 415

Val Ala Thr Leu Ile Asp Arg Phe Val Lys Gly Arg Gly Gln Leu Asp
            420                 425                 430

Lys Asp Thr Leu Asp Thr Leu Thr Ala Phe Tyr Pro Gly Tyr Leu Cys
        435                 440                 445

Ser Leu Ser Pro Glu Glu Leu Ser Ser Val Pro Pro Ser Ser Ile Trp
    450                 455                 460

Ala Val Arg Pro Gln Asp Leu Asp Thr Cys Asp Pro Arg Gln Leu Asp
465                 470                 475                 480

Val Leu Tyr Pro Lys Ala Arg Leu Ala Phe Gln Asn Met Asn Gly Ser
                485                 490                 495

Glu Tyr Phe Val Lys Ile Gln Ser Phe Leu Gly Gly Ala Pro Thr Glu
            500                 505                 510

Asp Leu Lys Ala Leu Ser Gln Gln Asn Val Ser Met Asp Leu Ala Thr
        515                 520                 525

Phe Met Lys Leu Arg Thr Asp Ala Val Leu Pro Leu Thr Val Ala Glu
    530                 535                 540

Val Gln Lys Leu Leu Gly Pro His Val Glu Gly Leu Lys Ala Glu Glu
545                 550                 555                 560

Arg His Arg Pro Val Arg Asp Trp Ile Leu Arg Gln Arg Gln Asp Asp
                565                 570                 575

Leu Asp Thr Leu Gly Leu Gly Leu Gln Gly Gly Ile Pro Asn Gly Tyr
            580                 585                 590

Leu Val Leu Asp Leu Ser Val Gln Glu Thr Leu Ser Gly Thr Pro Cys
```

```
            595                 600                 605
Leu Leu Gly Pro Gly Pro Val Leu Thr Val Leu Ala Leu Leu Leu Ala
    610                 615                 620

Ser Thr Leu Ala
625
```

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Gly Gly Gly Gly Ser
1               5
```

(2) INFORMATION FOR SEQ ID NO: 4:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

```
Arg Glu Asp Leu Lys
1               5
```

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

```
Arg Glu Asp Leu
1
```

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

```
Arg Asp Glu Leu
1
```

(2) INFORMATION FOR SEQ ID NO: 7:

(i) SEQUENCE CHARACTERISTICS:
        (A) LENGTH: 4 amino acids
        (B) TYPE: amino acid
        (C) STRANDEDNESS: <Unknown>

```
        (D) TOPOLOGY: linear (ii) MOLECULE TYPE: peptide (xi) SEQUENCE DESCRIPTION: SEQ ID NO: 7:

Lys Asp Glu Leu
1

(2) INFORMATION FOR SEQ ID NO: 8:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Arg Pro Arg Phe Arg Arg
1               5
```

MESOTHELIN, IMMUNOGENIC PEPTIDES DERIVED THEREFROM, AND COMPOSITIONS COMPRISING MESOTHELIN, OR IMMUNOGENIC PEPTIDES THEREOF

This application is a divisional of U.S. application Ser. No. 09/215,035, filed Dec. 17, 1998, now U.S. Pat. No. 6,153,430 which is a divisional of U.S. application Ser. No. 08/776,271, filed Jan. 12, 1998, now U.S. Pat. No. 6,083,502 which is a national stage filing under 35 U.S.C. § 371 of PCT/US97/00224, filed Jan. 3, 1997, which claims priority from U.S. Provisional Application No. 60/010,166, filed Jan. 5, 1996, all of which are hereby incorporated by reference.

FIELD OF THE INVENTION

This invention relates to the identification of a specific antigen found on tumor cells, particularly mesotheliomas and ovarian tumor cells and, inter alia, methods and compositions for targeting cells bearing the antigen.

BACKGROUND OF THE INVENTION

Monoclonal antibodies are currently being used to diagnose and treat cancer (Mach, J., et al., *Current Opinion Immunol.* B, 685-693 (1991); Grossbard, M. L., et al., *Blood* 80 (4):863-878 (1992)). To be useful for therapy, the antibody should recognize an antigen that is present in large amounts on the cancer cells and in negligible amounts in normal cells. Alternatively the antigen can be present in substantial amounts on normal cells, if the normal cells are not components of an essential organ. This approach has been useful in developing new treatments for leukemias and lymphomas. Several differentiation antigens have been identified on lymphomas and leukemias which are good targets for immunotherapy, because they are not present on the stem cells which give rise to differentiated lymphocytes (Grossbard, M. L., et al., *Blood* 80 (4):863-878 (1992)). Thus, normal lymphocytes that are killed by immunotherapy can be regenerated. Some examples of lymphocyte antigens of this type are CD19, CD22, CD25 and CD30 (Grossbard, M. L., et al., *Blood* 80 (4):863-878 (1992); Engert, A., et al., *Cancer Research* 50, 84-88 (1990)). Clearly, it would be very useful to have antibodies that recognize differentiation antigens on solid tumors, but only a small number of these are available. One reason contributing to the paucity of such antibodies is that efforts to identify differentiation antigens on various types of epithelial cells have been relatively modest compared with the intense efforts made to identify differentiation antigens on cells of the hematopoietic system.

Ovarian cancer represents one of the diseases which could be treated by immunotherapy, because the ovaries are always removed during surgery for this disease and reactivity with normal ovarian tissue is not a problem. Several antibodies that recognize differentiation antigens on ovarian cancer cells have been generated. One of these is OC125 that recognizes the CA125 antigen (Bast, R., et al., *N. Eng. J. Med.* 309, 883-887 (1983)). CA125 is a high molecular weight glycoprotein that is shed by ovarian cancer cells and has been useful in the diagnosis of ovarian cancer. However, antibodies to CA125 are not useful for immunotherapy because the CA125 antigen is shed into the blood stream (Bast, R., et al., *N. Eng. J. Med.* 309, 883-887 (1983)). Another is MOV18 which recognizes the folate binding protein. This protein is abundant in ovarian cancers as well as in some other tumors. Unfortunately, this protein is also abundantly expressed in kidney (Campbell, I. G., et al., *Cancer Res.* 51, 5329-5338 (1991)). An antibody we previously isolated and termed MAb K1 reacts with many ovarian cancers and many mesotheliomas. Like OC125, the antibody also reacts with normal mesothelial cells, but it does not react with other cell types except for weak reactivity with some cells in the trachea (Chang, K., et al., *Int. J. Cancer* 50, 373-381 (1992); Chang, K., et al., *Cancer Res.* 52, 181-186 (1992), see also U.S. Pat. No. 5,320,956). The antigen recognized by MAb K1 appears to be a differentiation antigen present on mesothelium and is expressed on cancers derived from mesothelium such as epithelioid type mesotheliomas as well as on most ovarian cancers. Thus immunotherapy directed at the CAK1 antigen should take into account the potential risk of damaging normal mesothelial cells and perhaps cells of the trachea (Chang, K., et al., *Int. J. Cancer* 50, 373-381 (1992); Chang, K., et al., *Cancer Res.* 52, 181-186 (1992); Chang, K., et al., *Int. J. Cancer* 51, 548-554 (1992); Chang, K., et al., *Am. J. Surg. Pathol.* 16, 259-268 (1992)).

Using the ovarian cancer cell line OVCAR-3 as well as HeLa cells, the antigen has been shown to be an approximately 40 kD glycoprotein that is attached to the cell surface by phosphatidylinositol. The protein is released when cells are treated with phosphotidylinositol specific phospholipase C (Chang, K., et al., *Cancer Res.* 52, 181-186 (1992)). We had previously attempted to clone a cDNA encoding the CAK1 antigen but instead cloned cDNAs encoding two different intracellular proteins which also react with MAb K1 (Chang, K., and Pastan, I., *Int. J. Cancer* 57, 90-97 (1994)). Neither of these is the cell surface membrane antigen recognized by MAb K1.

SUMMARY OF THE INVENTION

The present invention provides uses for isolated polypeptides comprising at least 10 contiguous amino acids from the polypeptide sequence of SEQ ID NO: 2, wherein the polypeptide binds to antisera raised against the full-length polypeptide of SEQ ID NO: 2 as an immunogen, which has been fully immunoadsorbed with a 40 kD polypeptide attached to the cell surface of OVCAR-3 and HeLa cells (the K1 antigen). Full-length polypeptides of the invention are typically about 69 kD in size, although they are larger when glycosylated or incorporated into a construct such as an eukaryotic expression vector. The polypeptides of the present invention may be present in several forms, including isolated naturally occurring endoproteolytic polypeptides, recombinantly produced polypeptides, and as portions of recombinant polypeptides such as fusion proteins.

The present invention also provides uses for isolated nucleic acids which encode the polypeptides described above. Exemplary nucleic acids include those described in SEQ ID NO: 1. In preferred embodiments, the nucleic acid is part of a recombinant vector such as a plasmid or virus or may be used as a probe to detect for the antigen. In preferred embodiments, the nucleic acid selectively hybridizes to the nucleic acid of SEQ ID NO: 1. The nucleic acid sequence may encode, e.g., a mesothelin polypeptide with complete sequence identity to a naturally occurring mesothelin protein. The nucleic acid may also encode a mesothelin polypeptide which is not identical to a naturally occurring mesothelin polypeptide, such as a fusion protein, or a genetically engineered mutant mesothelin protein which retains the bases critical for protein function or immunogenicity as described herein.

Recombinant cells which comprise a nucleic acid of the present invention are also provided, including eukaryotic and prokaryotic cells. The present invention also provides antibodies which bind specifically to the polypeptides of the present invention.

The invention further provides methods for targeting and/or inhibiting the growth of cells bearing mesothelin; methods for detecting the antigen and its expression level as an indication of the presence of tumor cells; and kits for such detection.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "antibody" as used herein, includes various forms of modified or altered antibodies, such as an intact immunoglobulin, various fragments such as an Fv fragment, an Fv fragment containing only the light and heavy chain variable regions, an Fv fragment linked by a disulfide bond (Brinkmann, et al. *Proc. Natl. Acad. Sci. USA*, 90: 547-551 (1993)), an Fab or (Fab)'$_2$ fragment containing the variable regions and parts of the constant regions, a single-chain antibody and the like (Bird et al., *Science* 242: 424-426 (1988); Huston et al., *Proc. Nat. Acad. Sci. USA* 85: 5879-5883 (1988)). The antibody may be of animal (especially mouse or rat) or human origin or may be chimeric (Morrison et al., *Proc Nat. Acad. Sci. USA* 81: 6851-6855 (1984)) or humanized (Jones et al., *Nature* 321: 522-525 (1986), and published UK patent application #8707252).

The term "immunoassay" is an assay that utilizes an antibody to specifically bind an analyte or antigen. The immunoassay is characterized by the use of specific binding properties of a particular antibody to isolate, target, and/or quantify the analyte.

The terms "isolated," "purified," or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The term "nucleic acid probe" refers to a molecule which binds to a specific sequence or subsequence of a nucleic acid. A probe is preferably a nucleic acid which binds through complementary base pairing to the full sequence or to a subsequence of a target nucleic acid. It will be understood by one of skill in the art that probes may bind target sequences lacking complete complementarity with the probe sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "recombinant" when used with reference to a cell indicates that the cell encodes a DNA whose origin is exogenous to the cell-type. Thus, for example, recombinant cells express genes that are not found within the native (non-recombinant) form of the cell.

The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" or "substantial similarity" in the context of a polypeptide indicates that a polypeptide comprises a sequence with at least 70% sequence identity to a reference sequence, or preferably 80%, or more preferably 85% sequence identity to the reference sequence, or most preferably 90% identity over a comparison window of about 10-20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The phrases "specifically binds to a protein" or "specifically hybridizes to" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies*, A Laboratory Manual, Cold Spring Harbor Publications, New York, for a description of immunoassay formats and conditions that can be used to determine specific immunoreactivity.

BRIEF DESCRIPTION OF THE DRAWINGS

FIG. 1: Nucleotide sequence (SEQ ID NO:1) and deduced amino acid sequence (SEQ ID NO:2) of the CAK1-9 cDNA. The nucleotide sequence (upper line) and the deduced amino acid sequence (lower line) of the CAK1 cDNA is listed with nucleotide numbers at left. The translation of CAK1 starts at nucleotides 100-102 (ATG) and terminates at 1986-88 (TGA). The putative signal peptide is underlined and a typical hydrophobic sequence for GPI anchorage is double-underlined. A likely furin cleavage site RPRFRR is underlined and the cleavage site shown by an arrow. There are four potential N-linked glycosylation sites (in bold letters). A variant polyadenylation signal (AGTAAA) is present 22 base pairs upstream from the polyadenylation tail. The original p6-1 cDNA sequence spans nucleotides 721 to 213.

DETAILED DESCRIPTION

Figure 2:
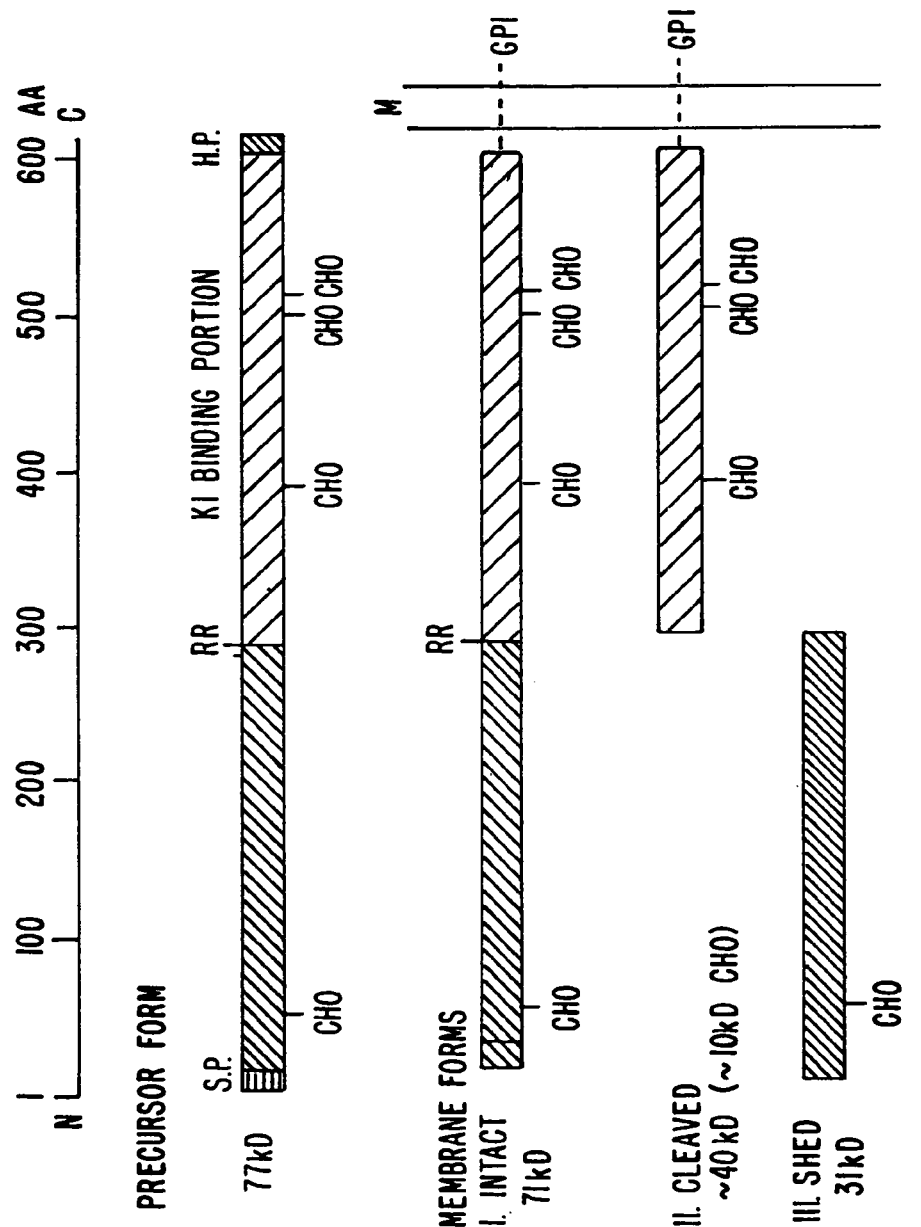
FIG. 2: Different forms of the CAK1 tumor antigen. S.P.=putative signal peptide; H.P.=GPI anchorage dependent hydrophobic peptide; CHO=carbohydrates; M=membrane, AA=amino acids.

This invention relates to the discovery of an antigen, referred to herein mesothelin, found on mesothelium, mesotheliomas, ovarian cancer cells and some squamous cell carcinomas. Previously, an antibody designated monoclonal antibody K1 was described which reacts with an antigen found on OVCAR-3 cells (from a human ovarian tumor cell line) having a molecular weight of 40 kD (kilodaltons). e.g. U.S. Pat. No. 5,320,956. The antigen described and claimed here was unexpectedly obtained during an attempt to clone and sequence the K1 antigen. Mesothelin in its full-length form has an apparent molecular weight of about 69 kD and appears to be the precursor protein for the 40 kD K1 antigen. The K1 antigen itself proved difficult to clone and our first attempts resulted in the cloning of two different intracellular proteins as mentioned above (see Chang & Pastan, Int. J. Cancer, supra). Though the existence of the K1 antigen was known, its cDNA was not routine to clone. First, we were not able to obtain sufficient amounts of it to clone. The methods used here were more laborious, but successful because unbeknownst to us the K1 antigen was derived from a larger molecule that we did not know existed. The DNA sequence and corresponding amino acid sequence for full-length mesothelin are set out in FIG. 1 and in SEQ ID NOS: 1 and 2, respectively.

Reference to mesothelin herein refers to both the isolated full-length polypeptide and isolated polypeptide fragments of at least 10 contiguous amino acids from the full-length sequence wherein the fragment binds to antisera raised against the full-length polypeptide, which has been fully immunosorbed with the 40 kD K1 antigen.

Mesothelin, as described here represents an antigen which is found on mesothelium, mesotheliomas, ovarian cancers and some squamous cell carcinomas. We have designated this antigen mesothelin to reflect its presence on mesothelial cells. The full-length cDNA for mesothelin is 2138 bp in length and contains an open reading frame of 1884 bp. The protein it encodes contains 628 amino acids with a calculated molecular weight of about 69000 daltons in its full-length form.

The protein contains four potential N-linked glycosylation sites N-X-S or N-X-T that are shown in bold letters in FIG. 1. A typical signal sequence is not present at the amino terminus. However, a short hydrophobic segment is located 15 amino acids from the first methionine (FIG. 1). This sequence might function as a signal sequence for membrane insertion, because the protein is found on the cell surface and is inserted into microsomes during cell free translation. Also present is a putative proteolytic processing site, RPRFRR, beginning at amino acid 293 (FIG. 1). This site is recognized by furin, a protease important in the processing of several membrane proteins as well as in the activation of *Pseudomonas* and diphtheria toxins (Chiron, M. F., et al., *J.B.C.* 269(27):18169-18176 (1994)).

The 40 kD form ("K1") appears to be derived from a 69 kD precursor by several processing steps. These are summarized in FIG. 2. Initially, mesothelin is made as a 69 kD polypeptide with a hydrophobic tail which is probably removed and replaced by phosphatidylinositol (Chang, K., et al., *Cancer Res.* 52, 181-186 (1992)). After glycosylation at one or more of its four putative N-linked glycosylation sites, it is cleaved by a protease to yield higher molecular weight forms, the 40 kD fragment (or doublet) found on the surface of OVCAR-3 cells and a smaller (~31 kD) fragment. The latter could be released into the medium and/or further degraded. We found that the amino terminal fragment was detected in the medium of OVCAR-3 cells.

Mesothelin is one of many proteins and glycoproteins that are attached to the cell surface by phosphatidylinositol. Several functions have been ascribed to these molecules. Some are receptors involved in cell signaling; others are involved in cellular recognition and/or adhesion (Dustin, M. L., et al., *Nature* 329, 846-848 (1987); Stiernberg, J., et al., *J. Immunol.* 38, 3877-3884 (1987)). GPI linked proteins may interact with tyrosine kinases (Stefanova, I., et al., *Science* 254, 1016-1019 (1991); Pandey, A., et al., *Science* 268, 567-569 (1995)). Antibodies to mesothelin would be useful in inhibiting the spread or implantation of ovarian cancer cells into the peritoneal wall that sometimes occurs, for example, during ovarian cancer surgery. Without intending to be bound by theory, it is our belief that mesothelin is likely responsible for the adhesion and implantation of ovarian carcinoma cells that frequently occurs throughout the peritoneal cavity or the adhesion of tumor cells in the thoracic cavity. Mesothelin plays a role in adhesion since mesothelin transfectants are more slowly removed from culture dishes than non-transfected cells. Mesothelial cells are extremely flat and regulate the traffic of molecules and cells in and out of the peritoneal or thoracic cavity.

Mesothelin is very abundant in normal mesothelial cells from which malignant mesotheliomas and ovarian cystadenocarcinomas are derived. These two types of tumors share a unique biological characteristic that distinguishes them from other solid tumors. In the early stages, both types of tumors spread aggressively throughout the peritoneal (or thoracic) cavity and invade locally but do not metastasize distally through lymphatics or the blood stream. In fact, many patients succumb to their cancer before distant metastases develop. Mesothelin likely has a role in this process, since cells overexpressing mesothelin have altered adhesive properties and mesothelin expression is diminished in poorly differentiated ovarian cancers (Chang, K., et al., Int. J. Cancer 51, 548-554 (1992); Chang, K., et al., Am. J. Surg. Pathol. 16, 259-268 (1992)). Implantation of ovarian cancer cells through a strong adhesion mechanism may be the first step towards local invasion and distal metastasis. Thus, blocking ovarian cancer implantation will prevent invasion and metastasis as well as proliferation of the cancer cells and lead cancer cells to apoptosis and the like.

I. Detection for Mesothelin

The detection of mesothelin is useful as an indicator of the presence of tumor cells, particularly ovarian tumor cells or mesotheliomas. If found in serum it can be a factor indicating the presence of residual cancer cells. Tumor tissues contain various proteases which may be responsible for the cleavage of mesothelin. The amount of N-terminal fragment of mesothelin present in blood or ascitic fluid can reflect the number of residual tumor cells present. The serological detection of mesothelin may serve as a novel indicator for monitoring the process of disease. The basic principle for detection of the mesothelin proteins is to detect the protein using specific ligands that bind to mesothelin but not to other proteins or nucleic acids in a normal human cell or its environs. The ligands can be either nucleic acid or antibodies. The ligands can be naturally occurring or genetically or physically modified such as non-natural or antibody derivatives, i.e. FAB, or chimeric antibodies.

A. Sample Collection and Processing

Mesothelin is preferably quantified in a biological sample, such as a serum, cell, or a tissue sample derived from a patient. In a preferred embodiment, mesothelin is quantified in samples of serum, mesothelial cells, cervical tissue or ovarian tissue with reference to a standard prepared from recombinant mesothelin.

The sample may be pretreated as necessary by dilution in an appropriate buffer solution or concentrated, if desired depending upon the assay being used. Any of a number of standard aqueous buffer solutions, employing one of a variety of buffers, such as phosphate, Tris, or the like, at physiological pH can be used.

B. Quantification of Mesothelin Peptides.

Mesothelin peptides may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

C. General Techniques—Nucleic Acid Detection

Accepted means for conducting hybridization assays for detection are known and general overviews of the technology can be had from a review of: *Nucleic Acid Hybridization: A Practical Approach*, Ed. Hames, B. D. and Higgins, S. J., IRL Press, 1985; *Hybridization of Nucleic Acids Immobilized on Solid Supports*, Meinkoth, J. and Wahl, G.; *Analytical Biochemistry*, Vol 238, 267-284, 1984 and Innis et al., *PCR Protocols*, supra, all of which are incorporated by reference herein.

If PCR is used, for example, primers are designed to target a specific portion of the nucleic acid of the targeted agent. Preferably the primers are about 14 to about 24 nucleotides in length. From the sequence information provided herein, those of skill in the art will be able to select appropriate specific primers.

Target specific probes may be used in the nucleic acid hybridization diagnostic assays for mesothelin. The probes are specific for or complementary to the target of interest. For example, probes to one of the nucleic acid sequences in the open reading frame for mesothelin would be effective. For precise allelic differentiation, the probes should be about 14-nucleotides long and preferably about 20-30 nucleotides. For more general detection, nucleic acid probes are about 50 to about 1000 nucleotides, most preferably about 200 to about 400 nucleotides.

The detection of the mesothelin polypeptides and other aspects of the present invention may make use of techniques such as PCR, TAS, 3SR, QB amplification and cloning, to amplify a nucleic acid in a biological sample which encodes a mesothelin polypeptide for detection or for, inter alia, the production of probes and primer tools for detection.

The presence of mesothelin nucleic acid in a biological sample such as, for example, serum or tissue suspected to contain tumor cells, is useful, e.g., as a probe to assess the presence of mesothelin and subsequently provide evidence indicative of tumor cells.

The nucleic acids of the present invention are cloned, or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnhein & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117.

It will be readily understood by those of skill in the art and it is intended here, that when reference is made to particular sequence listings, such as SEQ ID NOS: 1 and 2, such reference includes sequences which substantially correspond to its complementary sequence and those described including allowances for minor sequencing errors, single base changes, deletions, substitutions and the like, such that any such sequence variation corresponds to the nucleic acid sequence to which the relevant sequence listing relates.

D. Antibodies to Mesothelin and Antibody-Ligand Binding Assays

Antibodies (or antisera) are raised to the polypeptides of the present invention, including individual fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

1. Antibody Production

A number of immunogens are used to produce antibodies specifically reactive with mesothelin polypeptides. Recombinant or synthetic polypeptides of 10 amino length, or greater, selected from sub-sequences of SEQ ID NO: 1 are the preferred polypeptide immunogen for the production of monoclonal or polyclonal antibodies. In one class of preferred embodiments, an immunogenic peptide conjugate is also included as an immunogen. Naturally occurring polypeptides are also used either in pure or impure form. Transfected mammalian cells overexpressing recombinant mesothelin can also be used as an immunogen, either in whole intact cells or membrane preparations. These immunogens are useful for polyclonal or monoclonal antibody generation.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animals immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, NY; and Harlow and Lane (1989) Antibodies: A Laboratory Manual Cold Spring Harbor Press, NY, which are incorporated herein by reference, and the examples below.

Antibodies, including binding fragments and single chain recombinant versions thereof, against predetermined fragments of mesothelin polypeptides are raised by immunizing animals, e.g., with conjugates of the fragments with carrier proteins as described above. Typically, the immunogen of interest is a peptide of at least about 3 amino acids, more typically the peptide is 5 amino acids in length, preferably, the fragment is 10 amino acids in length and more preferably the fragment is 15 amino acids in length or greater. The peptides are typically coupled to a carrier protein (e.g., as a fusion protein), or are recombinantly expressed in an immunization or expression vector. Antigenic determinants on peptides to which antibodies bind are typically 3 to 10 amino acids in length.

Monoclonal antibodies are prepared from cells secreting the desired antibody. These antibodies are screened for binding to normal or modified polypeptides. Specific monoclonal and polyclonal antibodies will usually bind with a $K_D$ of at least about 0.1 mM, more usually at least about 50 µM, and most preferably at least about 1 µM or better.

In some instances, it is desirable to prepare monoclonal antibodies from various mammalian hosts, such as mice, rodents, primates, humans, etc. Description of techniques for preparing such monoclonal antibodies are well known and are found in, e.g., Asai, ed. *Antibodies in Cell Biology*, Academic Press, Inc., San Diego, Calif.; Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495-497. The polypeptides and antibodies of the present invention are used with or without modification, and include chimeric antibodies such as humanized murine antibodies.

Other suitable techniques involve selection of libraries of recombinant antibodies in phage or similar vectors. See, Huse et al. (1989) *Science* 246: 1275-1281; and Ward, et al. (1989) Nature 341: 544-546.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, for example, Cabilly, U.S. Pat. No. 4,816,567; and Queen et al. (1989) *Proc. Nat'l Acad. Sci. USA* 86: 10029-10033.

The antibodies of this invention are also used for affinity chromatography in isolating mesothelin polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified mesothelin polypeptides are released.

The antibodies can be used to screen expression libraries for particular expression products such as mammalian mesothelin. Usually the antibodies in such a procedure are labeled with a moiety allowing easy detection of presence of antigen by antibody binding.

Antibodies raised against mesothelin polypeptides can also be used to raise anti-idiotypic antibodies. These are useful for detecting or diagnosing various pathological conditions related to the presence of the respective antigens.

2. Immunoassays

A particular protein can be quantified by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide Academic Press*, Orlando, Fla.; Price and Newman (eds.) (1991) *Prin-

*ciples and Practice of Immunoassays* Stockton Press, NY; and Ngo (ed.) (1988) *Non-isotopic Immunoassays* Plenum Press, NY.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled mesothelin peptide or a labeled anti-mesothelin antibody. Alternatively, the labeling agent may be a third moiety, such as another antibody, that specifically binds to the antibody/mesothelin complex, or to a modified capture group (e.g., biotin) which is covalently linked to the mesothelin peptide or anti-mesothelin antibody.

In a preferred embodiment, the labeling agent is an antibody that specifically binds to the capture agent (anti-mesothelin). Such agents are well known to those of skill in the art, and most typically comprise labeled antibodies that specifically bind antibodies of the particular animal species from which the capture agent is derived (e.g., an anti-idiotypic antibody). Thus, for example, where the capture agent is a mouse derived anti-human mesothelin antibody, the label agent may be a goat anti-mouse IgG, i.e., an antibody specific to the constant region of the mouse antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non-immunogenic reactivity with immunoglobulin constant regions from a variety of species. See, generally Kronval, et al., (1973) *J. Immunol.*, 111:1401-1406, and Akerstrom, et al., (1985) *J. Immunol.*, 135:2589-2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

(a) Non-Competitive Assay Formats

Immunoassays for detecting mesothelin may be either competitive or noncompetitive. Noncompetitive immunoassays are assays in which the amount of captured analyte (in this case mesothelin) is directly measured. In one preferred "sandwich" assay, for example, the capture agent (e.g., anti-mesothelin antibodies) are bound directly to a solid substrate where they are immobilized. These immobilized antibodies then capture mesothelin present in the test sample. The mesothelin thus immobilized is then bound by a labeling agent, such as a second human mesothelin antibody bearing a label. Alternatively, the second mesothelin antibody may lack a label, but it may, in turn, be bound by a labeled third antibody specific to antibodies of the species from which the second antibody is derived.

Sandwich assays for mesothelin may be constructed. As described above, the immobilized anti-mesothelin specifically binds to mesothelin present in the sample. The labeled anti-mesothelin then binds to the already bound mesothelin. Free labeled anti-mesothelin is washed away and the remaining bound labeled anti-mesothelin is detected (e.g., using a gamma detector where the label is radioactive).

(b) Competitive Assay Formats

In competitive assays, the amount of analyte (e.g., mesothelin) present in the sample is measured indirectly by measuring the amount of an added (exogenous) analyte displaced (or competed away) from a capture agent (e.g., anti-mesothelin antibody) by the analyte present in the sample. In one competitive assay, a known amount of analyte is added to the sample and the sample is contacted with a capture agent, in this case an antibody that specifically binds the analyte. The amount of analyte bound to the antibody is inversely proportional to the concentration of analyte present in the sample.

In a particularly preferred embodiment, the capture agent is immobilized on a solid substrate. The amount of mesothelin bound to the capture agent is determined either by measuring the amount of mesothelin present in an mesothelin/antibody complex, or alternatively by measuring the amount of remaining uncomplexed mesothelin. The amount of mesothelin may be detected by providing a labeled mesothelin.

A hapten inhibition assay is another preferred competitive assay. In this assay, a known analyte, in this case mesothelin, is immobilized on a solid substrate. A known amount of anti-mesothelin antibody is added to the sample, and the sample is then contacted with the immobilized mesothelin. In this case, the amount of anti-mesothelin antibody bound to the immobilized mesothelin is proportional to the amount of mesothelin present in the sample. Again the amount of immobilized antibody is detected by detecting either the immobilized fraction of antibody or the fraction of the antibody that remains in solution. Detection may be direct where the antibody is labeled, or indirect by the subsequent addition of a labeled moiety that specifically binds to the antibody as described above.

(c) Generation of Pooled Antisera for Use in Immunoassays.

A mesothelin protein that specifically binds to or that is specifically immunoreactive with an antibody generated against a defined immunogen, such as an immunogen consisting of the amino acid sequence of SEQ ID NO: 2, is determined in an immunoassay. The immunoassay uses a polyclonal antiserum which was raised to the protein of SEQ ID NO: 2 (the immunogenic polypeptide).

In order to produce an antisera for use in an immunoassay, the polypeptide of SEQ ID NO: 2 is isolated as described herein. For example, recombinant protein can be produced in a mammalian or other eukaryotic cell line. An inbred strain of mice is immunized with the protein of SEQ ID NO: 2 using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against proteins of interest, using a competitive binding immunoassay such as the one described in Harlow and Lane, supra, at pages 570-573.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with the protein of interest are combined and pooled. The cross-reacting antibodies are then removed from the pooled antisera by immunoadsorbtion. The immunoadsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunoadsorbed with the immunogenic polypeptide until no binding to the polypeptide used in the immunoadsorbtion is detectable. The fully immunoadsorbed antisera is then tested for reactivity with the test polypeptide. If no reactivity is observed, then the test polypeptide is specifically bound by the antisera elicited by the immunogenic protein.

D. Other Assay Formats

Western blot analysis can also be used to detect and quantify the presence of mesothelin in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind mesothelin. The anti-mesothelin antibodies specifically bind to mesothelin on the solid support. These antibodies may be directly labeled or alternatively may be subsequently detected using labeled antibodies (e.g., labeled sheep anti-mouse antibodies where the antibody to mesothelin is a murine antibody) that specifically bind to the anti-mesothelin.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) Amer. Clin. Prod. Rev. 5:34-41), which is incorporated herein by reference.

E. Labels

The labeling agent for the applications described herein can be, e.g., a monoclonal antibody, a polyclonal antibody, a mesothelin binding protein or complex such as those described herein, or a polymer such as an affinity matrix, carbohydrate or lipid. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3H$, $^{125}$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

F. Substrates

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082, which are incorporated herein by reference.

II. Targeting Effector Molecules to Mesothelin

This invention also provides for compositions and methods for detecting the presence or absence of tumor cells bearing mesothelin. These methods involve providing a chimeric molecule comprising an effector molecule, that is a detectable label attached to a targeting molecule that specifically binds mesothelin. The mesothelin targeting moiety specifically binds the chimeric molecule to tumor cells which are then marked by their association with the detectable label. Subsequent detection of the cell-associated label indicates the presence of a tumor cell.

In yet another embodiment, the effector molecule may be another specific binding moiety such as an antibody, a growth factor, or a ligand. The chimeric molecule will then act as a highly specific bifunctional linker. This linker may act to bind and enhance the interaction between cells or cellular components to which the fusion protein binds. Thus, for example, where the "targeting" component of the chimeric molecule comprises a polypeptide that specifically binds to mesothelin and the "effector" component is an antibody or antibody fragment (e.g. an Fv fragment of an antibody), the targeting component specifically binds cancer cells, while the effector component inhibits cell growth or may act to enhance and direct an immune response toward target cancer cells.

In still yet another embodiment the effector molecule may be a pharmacological agent (e.g. a drug) or a vehicle containing a pharmacological agent. Thus, the moiety that specifically binds to mesothelin may be conjugated to a drug such as vinblastine, doxirubicin, genistein (a tyrosine kinase inhibitor), an antisense molecule, and other pharmacological agents known to those of skill in the art, thereby specifically targeting the pharmacological agent to tumor cells.

Alternatively, the targeting molecule may be bound to a vehicle containing the therapeutic composition. Such vehicles include, but are not limited to liposomes, micelles, various synthetic beads, and the like.

One of skill in the art will appreciate that the chimeric molecules of the present invention may include multiple targeting moieties bound to a single effector or conversely, multiple effector molecules bound to a single targeting moiety. In still other embodiments, the chimeric molecules may include both multiple targeting moieties and multiple effector molecules. Thus, for example, this invention provides for "dual targeted" cytotoxic chimeric molecules in which targeting molecule that specifically binds to mesothelin is attached to a cytotoxic molecule and another molecule (e.g. an antibody, or another ligand) is attached to the other terminus of the toxin. Such a dual-targeted cytotoxin might comprise a growth factor substituted for domain Ia, for example, at the amino terminus of a PE and anti-TAC(Fv) inserted in domain III, between amino acid 604 and 609. Other antibodies may also be suitable.

A. The Targeting Molecule

In a preferred embodiment, the targeting molecule is a molecule that specifically binds to mesothelin. A variety of immunoassay formats may be used to select appropriate antibodies and are discussed above.

B. The Effector Molecule

As described above, the effector molecule component of the chimeric molecules of this invention may be any molecule whose activity it is desired to deliver to cells that express mesothelin. Particularly preferred effector molecules include cytotoxins such as PE or DT, radionuclides, ligands such as growth factors, antibodies, detectable labels such as fluorescent or radioactive labels, and therapeutic compositions such as liposomes and various drugs.

1. Cytotoxins

Particularly preferred cytotoxins include *Pseudomonas* exotoxins, *Diphtheria* toxins, ricin, and abrin. *Pseudomonas* exotoxin and *Diphtheria* toxin are most preferred.

(a) *Pseudomonas* Exotoxin (PE)

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al., *J. Biol. Chem.* 264: 14256-14261 (1989), incorporated by reference herein.

Where the targeting molecule is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO: 3).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include REDLK (SEQ ID NO:4) (as in native PE), REDL (SEQ ID NO: 5), RDEL (SEQ ID NO: 6), or KDEL (SEQ ID NO: 7), repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87:308-312 and Seetharam et al, *J. Biol. Chem.* 266: 17376-17381 (1991) and commonly assigned, U.S. Ser. No. 07/459,635 filed Jan. 2, 1990, all of which are incorporated by reference herein.

Deletions of amino acids 365-380 of domain Ib can be made without loss of activity. Further, amino acids 1-279 may be deleted so that the toxin begins with a methionine followed by glycine at position 280. A serine may be placed at position 289 to prevent formation of improper disulfide bonds is beneficial. The targeting molecule may be inserted in replacement for domain Ia.

Preferred forms of PE contain amino acids 253-364 and 381/608, and are followed by the native sequences REDLK (SEQ ID NO: 4) or the mutant sequences KDEL (SEQ ID NO: 7) or RDEL (SEQ ID NO: 6). Lysines at positions 590 and 606 may or may not be mutated to glutamine.

The targeting molecule may also be inserted at a point within domain III of the PE molecule. Most preferably the targeting molecule is fused between about amino acid positions 607 and 609 of the PE molecule. This means that the targeting molecule is inserted after about amino acid 607 of the molecule and an appropriate carboxyl end of PE is recreated by placing amino acids about 604-613 of PE after the targeting molecule. Thus, the targeting molecule is inserted within the recombinant PE molecule after about amino acid 607 and is followed by amino acids 604-613 of domain III. The targeting molecule may also be inserted into domain Ib to replace sequences not necessary for toxicity. Debinski, et al. *Mol. Cell. Biol.,* 11: 1751-1753 (1991).

Methods of cloning genes encoding PE fused to various ligands are well known to those of skill in the art. See, for example, Siegall et al., *FASEB J.,* 3: 2647-2652 (1989); Chaudhary et al. *Proc. Natl. Acad. Sci. USA,* 84: 4538-4542 (1987), which are incorporated herein by reference.

Those skilled in the art will realize that additional modifications, deletions, insertions and the like may be made to the chimeric molecules of the present invention or to the nucleic acid sequences encoding mesothelin-directed chimeric molecules. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

(b) *Diphtheria* Toxin (DT)

Like PE, diphtheria toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science,* 175: 901-903 (1972); Uchida et al. *J. Biol. Chem.,* 248: 3838-3844 (1973)).

In a preferred embodiment, the targeting molecule-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed. Chaudhary, et al., *Bioch. Biophys. Res. Comm.,* 180: 545-551 (1991).

Like the PE chimeric cytotoxins, the DT molecules may be chemically conjugated to a mesothelin targeting molecule, but, in a preferred embodiment, the targeting molecule will be fused to the *Diphtheria* toxin by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. *J. Biol. Chem.* 265: 11885-11889 (1990) and copending patent application (U.S. Ser. No. 07/620,939) which describe the expression of a number of growth-factor-DT fusion proteins.

The term "*Diphtheria* toxin" (DT) as used herein refers to full length native DT or to a DT that has been modified. Modifications typically include removal of the targeting domain in the B chain and, more specifically, involve truncations of the carboxyl region of the B chain.

Detectable labels suitable for use as the effector molecule component of the chimeric molecules of this invention include any composition detectable by spectroscopic, photochemical, biochemical, immunochemical, electrical, optical or chemical means all as described above.

C. Attachment of the Targeting Molecule to the Effector Molecule

One of skill will appreciate that the targeting molecule and effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

D. Conjugation of the Effector Molecule to the Targeting Molecule

In one embodiment, the targeting molecule is chemically conjugated to the effector molecule (e.g. a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071-4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann, *Science,* 252: 1657 (1991), U.S. Pat. Nos. 4,545,985 and 4,894,443 which are incorporated herein by reference.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

E. Production of Fusion Proteins

Where the targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.,* 85: 2149-2156 (1963), and Stewart et al., *Solid Phase Peptide Synthesis, 2nd ed*. Pierce Chem. Co., Rockford, Ill. (1984) which are incorporated herein by reference.

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention may be prepared by any suitable method, including, for example, cloning and restriction of appropriate sequences or direct chemical synthesis by methods such as the phosphotriester method of Narang et al. *Meth. Enzymol.* 68: 90-99 (1979); the phosphodiester method of Brown et al., *Meth. Enzymol.* 68: 109-151 (1979); the diethylphosphoramidite method of Beaucage et al., *Tetra. Lett.,* 22: 1859-1862 (1981); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids and vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182: *Guide to Protein Purification.*, Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

III. Administration to Patients of Targeting Agents to Mesothelin

Therapeutic agents of the present invention, such as antibodies to mesothelin or such as antibodies or other targeting molecules attached to an effector molecule are administered in any suitable manner, preferably with pharmaceutically acceptable carriers. One skilled in the art will appreciate that suitable methods of administering such compounds in the context of the present invention to a patient are available, and, although more than one route can be used to administer a particular compound, a particular route can often provide a more immediate and more effective reaction than another route. It should be recognized that the administration of peptides are well-known for a variety of diseases, and one of skill is able to extrapolate the information available for use of peptides to treat these other diseases to mesothelin peptides.

Pharmaceutically acceptable carriers are also well known to those who are skilled in the art. The optimal choice of carrier will be determined in part by the particular compound, as well as by the particular method used to administer the composition. Accordingly, there is a wide variety of suitable formulations of the pharmaceutical compositions of the present invention.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously, intrathecally or intraperitoneally or into vascular spaces, particularly into the peritoneal cavity or thoracic cavity, e.g., injection at a dosage of greater than about 1 μg/cc fluid/day. A permanent intrathecal catheter would be a convenient means to administer therapeutic antibodies. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared. Antibody or immunotoxin may also be administered via microspheres, liposomes or other microparticulate delivery systems placed in certain tissues including blood.

Dosages

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of the disease without producing unacceptable toxicity to the patient.

A therapeutically effective amount of the compound is that which provides either subjective relief of a symptom(s) or an objectively identifiable improvement, such as inhibition of tumor-cell growth, as noted by the clinician or other qualified observer. The dosing range varies with the compound used, the route of administration and the potency of the particular compound.

IV. Gene Therapy and Inhibitory Nucleic Acid Therapeutics

Using the nucleotide sequence information of this invention, one skilled in the art can formulate strategies and methods to isolate the mesothelin gene, describe the gene structure for function, and may also discover specific promoters for known or unknown transcriptional factors which may be of further value in the genetic intervention of mesothelioma and ovarian cancers. Analytical DNA sequencing of normal mesothelin in mesothelial cells may lead to a discovery of mutation(s) of the gene in mesothelioma and ovarian cancers.

Mesothelin manifests an adhesive property which can be attributed to implantation of the mesothelioma and ovarian cancers. By introducing antisense DNA or blocking the transcription of mesothelin gene, novel gene therapy regimens can be set up according to current strategies of gene therapy.

Inhibitory nucleic acid therapeutics which can block the expression or activity of the mesothelin gene will be useful in slowing or inhibiting the growth of mesotheliomas or ovarian tumors or other abnormal cells which are associated with mesothelin. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of, for example, a mesothelin gene. These different types of inhibitory nucleic acid technology are described in Helene, C. and Toulme, J., 1990, Biochim. Biophys. Acta. 1049:99-125, which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al., 1988, PNAS (USA) 85:1028-1032 and Harel-Bellan, A., et al., 1988, Exp. Med. 168:2309-2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be accomplished by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

This invention relates to the targeting of inhibitory nucleic acids to sequences of mesothelin for use in inhibiting or slowing the growth of tumors associated with mesothelin. A problem associated with inhibitory nucleic acid therapy is the effective delivery of the inhibitory nucleic acid to the target cell in vivo and the subsequent internalization of the inhibitory nucleic acid by that cell. Delivery, however, can be accomplished by linking the inhibitory nucleic acid to a targeting moiety to form a conjugate that binds to a specific receptor on the surface of the target infected cell, and which is internalized after binding. Preferably, the inhibitory nucleic acid will be delivered to the peritoneal cavity, the thoracic cavity, as well as any other location where cells bearing mesothelin are of interest.

Gene therapy can also correct genetic defects by insertion of exogenous cellular genes that encode a desired function into cells that lack that function, such that the expression of the exogenous gene a) corrects a genetic defect or b) causes the destruction of cells that are genetically defective. Methods of gene therapy are well known in the art, see, for example, Lu, M., et al. (1994), *Human Gene Therapy* 5:203; Smith, C. (1992), *J. Hematotherapy* 1:155; Cassel, A., et al. (1993), *Exp. Hematol.* 21-:585 (1993); Larrick, J. W. and Burck, K. L., GENE THERAPY: APPLICATION OF MOLECULAR BIOLOGY, Elsevier Science Publishing Co., Inc., New York, N.Y. (1991) and Kreigler, M. GENE TRANSFER AND EXPRESSION: A LABORATORY MANUAL, W.H. Freeman and Company, New York (1990), each incorporated herein by reference. One modality of gene therapy involves (a) obtaining from a patient a viable sample of primary cells of a particular cell type; (b) inserting into these primary cells a nucleic acid segment encoding a desired gene product; (c) identifying and isolating cells and cell lines that express the gene product; (d) re-introducing cells that express the gene product; (e) removing from the patient an aliquot of tissue including cells resulting from step c and their progeny; and (f) determining the quantity of the cells resulting from step c and their progeny, in said aliquot. The introduction into cells in step (b) of a vector that encodes a sequence (for a "desired gene product") which will block mesothelin expression or activity can be useful in inhibiting or slowing the growth of tumor cells associated with mesothelin.

V. Vaccine Development

Vaccine Development Using Mesothelin Amino Acid Sequence.

Substances suitable for use as vaccines for the prevention of and inhibition of the growth of tumors bearing mesothelin and methods for administering them may be employed. The vaccines are directed against mesothelin. Preferably, the vaccines comprise mesothelin derived antigen.

Vaccines can be made recombinantly. Typically, a vaccine will include from about 1 to about 50 micrograms of antigen or antigenic protein or peptide. More preferably, the amount of protein is from about 15 to about 45 micrograms. Typically, the vaccine is formulated so that a dose includes about 0.5 milliliters. The vaccine may be administered by any route known in the art. Preferably, the route is intraperitoneally or parenteral.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1:2-12 (1990).

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionibacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 µg to about 100 µg protein per patient. A preferable range is from about 1 µg to about 50 µg per dose. A more preferred range is about 15 µg to about 45 µg. A suitable dose size is about 0.5 ml. After formulation, the vaccine may be incorporated into a sterile container which is then sealed and stored at a low temperature, for example 4° C., or it may be freeze-dried. Lyophilization permits long-term storage in a stabilized form.

The treatment may consist of a single dose of vaccine or a plurality of doses over a period of time. It is preferred that the doses be given to a patient suspected of having mesothelin bearing tumor cells. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions within the amino acid sequence for mesothelin. For example, it is known in the protein art that certain amino acid residues can be substituted with amino acids of similar size and polarity without an undue effect upon the biological activity of the protein.

Using the mesothelin amino acid sequence information, one of skill in the art can perform epitope mapping against sera isolated from patients with ovarian cancers or mesotheliomas. Relatively strong epitopes may be identified and common epitope(s) may also be recognized. The epitope mapping against human sera can also be extended to a screening of epitope-peptides against activated human lymphocytes in order to identify potential T-cell epitopes. Theoretically, it is not likely that T-cell epitopes of mesothelin will be found in human T-cells, but mutations induced in mesothelin may create new epitopes which may be recognized by T-cells. Mutant mesothelin can easily be generated randomly using a phage display method. The resultant library is screened by human sera from patients suffering from malignant mesothelioma and ovarian cancer. Thus, suitable antigenic peptides may be identified for mesothelin-derived vaccines.

VI. Kits.

This invention further embraces diagnostic kits for detecting for the presence of mesothelin in tissue samples or in serum, comprising a container having a nucleic acid or an antibody or other targeting agent specific for mesothelin and instructional material for the detection of mesothelin.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification are herein incorporated by reference in their entirety for all purposes as if each individual publication or patent application were specifically and individually indicated to be incorporated by reference.

VI. Models for Evaluation of Therapies Directed to Mesothelin.

The mesothelin cDNA can be transfected into established tumor cell lines where it will express the protein. The transfected cell lines can be used to grow tumors in mice or other mammals to provide a model for testing therapies directed to controlling, suppressing or regulating mesothelin expression. Transfected tumor cell lines can be transplanted into the test mammal. The mammal can then be subjected to a drug of interest and subsequent tumor cell activity can be monitored to determine whether the drug of interest has anti-tumor effects. Tumor cell lines that have been found to be particularly good candidates for this procedure include, mouse NIH 3T3 cells (tumorigenic cell lines), A431 human ovarian tumor cells and MCF-7 breast tumor cells, A2780 human ovarian tumor cells and OVCAR-3 human epidermoid carcinoma cells.

EXAMPLES

A. Materials and Methods

1. Cells and antibodies. Human ovarian tumor cell line, OVCAR-3, and cell lines A431, KB, MCF-7, COS-1, WI-38 and NIH 3T3 were obtained from the American Type Culture Collections (ATCC, Rockville, Md.). Cells were cultured either in RPMI 1640 or DMEM media (GIBCO Laboratories, Grand Island, N.Y.), supplemented with L-glutamine (2 mM), penicillin (50 µg/ml), streptomycin (50 units/ml) and 5-10% fetal bovine serum (GIBCO). NIH 3T3 transfectants were grown in DMEM with 0.8 mg/ml of G418 (GIBCO). Cells were used when they reached 80-90% confluency after washing three times with ice-cold PBS (GIBCO). MAb K1 and antibody MOPC-21 have been described (Chang, K., et al., *Int. J. Cancer* 50, 373-381 (1992)) and were used in a concentration of 5-10 µg/ml.

2. Isolation of the cDNA clones. The HeLa S3 cDNA library (ClonTech, Palo Alto, Calif.) was screened at approximately 50,000 pfu/150 mm filter as described previously (Chang, K., and Pastan, I., *Int. J. Cancer* 57, 90-97 (1994)) using protein A-purified MAb K1 (5 µg/ml) and peroxidase-conjugated goat anti-mouse IgG (H+L) (10 µg/ml, Jackson ImmunoResearch Lab, Inc., West Grove, Pa.). Two positive plaques (λ6-1, λ6-2) were isolated and the phages were purified to homogeneity by three or more rounds of screening. After verification of their specificity with MAb K1 by showing they did not react with a control MOPC-21 antibody, single-plaque isolates of λ6-1 and λ6-2 were used to prepare 5 to 10 phage-plates, followed by extraction and purification of phage DNA with a lambda phage DNA kit (Qiagen, Inc., Chatsworth, Calif.). Phage DNA was then digested with EcoRI and the insert subcloned into the EcoRI site of a pcDNAI/Amp (Invitrogen Corporation, San Diego, Calif.) vector using a rapid ligation protocol (Chang, K., and Pastan, I., *Int. J. Cancer* 57, 90-97 (1994)). Plasmid DNAs were isolated using Qiagene's plasmid DNA isolation kit (Chang, K., and Pastan, I., *Int. J. Cancer* 57, 90-97 (1994)). Restriction mapping using XhoI, EcoRI, SalI, BamHI, NcoI, and DNA sequencing revealed that the two plasmid clones (p6-1 and p6-2) had identical 1500 base-pair inserts.

To isolate a longer clone, the insert of p6-1 was purified to make a cDNA probe (specific activity=$8.5 \times 10^5$ cpm/ml) by random priming. The HeLa S3 cDNA library was re-screened using the filter hybridization method described previously (Chang, K., and Pastan, I., *Int. J. Cancer* 57, 90-97 (1994)). 14 lambda clones were isolated and purified, and their insert sizes were assessed by digestion with EcoRI. Four large inserts were subcloned into a pcDNAI/Amp plasmid vector (p9, p13-1, p16 and p18-1). p9 contained the largest insert with a long open reading frame.

3. DNA sequencing analysis. Using T3 and T7 promoter primers and twenty 17 bp synthetic primers, the entire cDNA insert of p9 was sequenced using the method described by Sanger (Sanger, F., et al., *Proc. Natl. Acad. Sci. USA* 74, 5463-5467 (1977)) and an automatic cycle sequencing method.

4. Northern blot analysis. Total RNAs (20 µg) from OVCAR-3, KB, MCF-7, A431 and WI38 were electrophoresed on a 1% agarose gel in MOPS buffer with 16.6% formaldehyde, and then transferred to a Nylon paper. Northern hybridization was done with a method described before (Chang, K., and Pastan, I., *Int. J. Cancer* 57, 90-97 (1994)). The blot washed and reprobed with a $^{32}$P-labeled human β-actin cDNA as an internal control to assess the integrity and quantity of the RNA samples loaded.

5. In Vitro transcription and translation. TNT Coupled Reticulocyte Lysate System, canine pancreatic microsomal membrane, 2 µg of plasmid DNAs of p9 (pcDICAK1-9), pAPK1 (Chang, K., and Pastan, I., *Int. J. Cancer* 57, 90-97 (1994)), to eliminate and $^3$H leucine were used in an in vitro transcription/translation and translocation/processing experiment according to the protocol of the manufacturer (Promega, Madison, Wis., USA). Translation products were resolved on a 10% SDS-PAGE reducing gel. The proteins were fixed and the unincorporated label was removed by soaking the gel three times in 200 ml of buffer, 40% methanol and 10% acetic acid in deionized water for 30 min. The gels were then soaked for 30 min in 200 ml of INTENSIFY Part A and Part B (NEN Research Product, Boston, Mass.). After drying, the translated products were visualized by autoradiography.

6. Expression of the cloned cDNAs in mammalian cells. Transient transfections of COS cells were performed using pcDICAK1-9 (p9) and LipofectAMINE (GIBCO) following the manufacturer's protocol (GIBCO). COS1 cells were plated a day before the experiment at $2.5 \times 10^5$ cells/60 mm dish. 24 µl of LipofectAMINE and 76 µl of OptiMEMI medium were mixed with 10 µg of pcDNAI/Amp vector, or pcDICAK1-9 in 100 µl of OptiMEMI medium at room temperature for 30 min. After washing the COS-1 cells with OptiMEMI twice, 2.4 ml OptiMEMI were added to the transfection mixtures and overlaid onto COS1 cells, followed by incubation at 37° C. for 5 hours. 2.6 ml of DMEM with 20% FBS were then added into each dish. 48 hours after transfection, the dishes were subjected to immunofluorescence labeling as described (Chang, K., et al., *Int. J. Cancer* 50, 373-381 (1992); Chang, K., et al., *Cancer Res.* 52, 181-186 (1992)) or other treatments. The insert from plasmid p9 (in pcDNAI/Amp) was also subcloned into a pcDNA3 (Invitrogen) vector for stable transfection. Plasmid minipreps were made using Qiagen's Miniprep Plasmid DNA Kit and orientation of the insert in individual clone was determined by restriction mapping. The resulting plasmid, pcD3CAK1-9, was then used to transfect NIH 3T3, MCF-7, A431 and OVCAR-3 cells by DNA-calcium phosphate precipitation as described (Chen, C. and Okayama, H., *Mol. Cell. Biol.* 7, 2745-2752 (1987)). After overnight exposure to the precipitate, the cells were washed with PBS three times and fed with fresh DMEM/10% FBS medium for 2-3 days. Geneticin G418 sulfate (0.8 mg/ml) was added and the cultures were maintained until colonies of 2-3 mm in diameter were formed. Colonies were then transferred into wells of a 96 well plate and then into a 35 mm dish when they were 80% confluent. Transfected cells were screened by immunofluorescence (Chang, K., et al., *Int. J. Cancer* 50, 373-381 (1992); Chang, K., et al., *Cancer Res.* 52, 181-186 (1992)) and positive cells were further subcloned by limited dilution as described (Chang, K., et al., *Int. J. Cancer* 50, 373-381 (1992)). One of the NIH 3T3 transfectant clones, NIH 3T3 K20, was chosen for further study. To localize the expression of CAK1, both cell surface and intracellular immunofluorescence labeling was also performed according to methods described before (Chang, K., et al., *Cancer Res.* 52, 181-186 (1992)).

7. Treatment of the transfected cells with PI-PLC. CAK1 cDNA transfected NIH 3T3 cells (NIH 3T3 K20) were grown in 175 mm$^2$ flasks, and when they reached 90% confluency, the cells were washed in PBS for three times. The cells were incubated with either 5 ml of 1.25 U/ml PI-PLC (from *Bacillus cereus*; Boehringer Mannheim Biochemicals) or 0.05% trypsin/0.052 mM EDTA for 30 min at 37° C. and 30 min at room temperature with shaking. The supernatants were collected and after centrifugation at 1000×g and concentrated about 10 fold using Centricon 30 (Amicon, Inc., Beverly, Mass.). The concentrated supernatants were used in SDS-PAGE and immunoblot analysis. The enzyme-treated cells can be recultured and the recovery of CAK1 expression can be seen after overnight culture. Treatment with PI-PLC was done in a similar manner using 35 mm diameter dishes followed by immunofluorescence labeling of the treated cells (Chang, K., et al., *Cancer Res.* 52, 181-186 (1992)).

8. Immunoblotting analysis of the transfected NIH 3T3 cells. Membrane and cytosolic fractions from transfected NIH 3T3 K20 cells (Chang, K., and Pastan, I., *Int. J. Cancer* 57, 90-97 (1994)) were subjected to 12.5% SDS-PAGE and the resolved proteins were transferred to nitrocellulose. Immunoblotting was performed as previously described (Chang, K., et al., *Int. J. Cancer* 51, 548-554 (1992); Chang, K., and Pastan, I., *Int. J. Cancer* 57, 90-97 (1994)).

B. Results

Expression cloning was used to isolate the CAK1 cDNA. We previously observed that MAb K1 reacts with OVCAR-3 and HeLa cells. Because we were unable to isolate the cDNA from an OVCAR-3 library (Chang, K., and Pastan, I., *Int. J. Cancer* 57, 90-97 (1994)), we screened a HeLa cDNA library expressed in λgt11 as described above. A total of $1 \times 10^6$ phages were screened and two phage clones (λ6-1 and λ6-2) were identified. DNA sequencing showed both phages contained the same 1.5 kb insert. The insert hybridized to mRNA from OVCAR-3 and KB cells (a HeLa subclone which also reacts with MAb K1) but not to RNA from many other cell lines indicating that the cDNA is specific for cells reacting with MAb K1. 20 µg of total RNA from OVCAR-3 cells (lane 1), MCF-7 cells (lane 2), KB cells (a HeLa subclone, lane 3), A431 cells (lane 4) and WI38 cells (lane 5) were resolved by electrophoresis transferred to nylon paper and blotted with a $^{32}$P-labeled CAK1 probe. Hybridization with an actin probe showed that the lanes were equally loaded. The mRNA detected is 2.2 kb in size indicating that the insert isolated was not full length. The insert contained an open reading frame, a stop codon and a poly A tail but the 5' end appeared to be missing. Therefore, the phage library was rescreened with one of the inserts and 14 new phages with cDNA inserts of various sizes isolated. The largest insert (#9) was 2138 bp long and when sequenced contained an open reading frame of 1884 bp (FIG. 1). It contains a typical Kozak sequence (Kozak, M., *Nucleic Acids Res.* 5, 8125-8148 (1987)) (AXXATGG) followed by an open reading frame that encodes a 69 kD protein. The sequence was not present in various data bases examined (EMBL-GenBank). Because the CAK1 antigen was originally found to be about 40 kD in size, several experiments were carried out to determine if clone 9 encoded CAK1.

1. In vitro translation. Insert 9 was cloned into a pcDNAI/Amp vector to make pcDICAK1-9 and used in the TNT reticulocyte system. pcDICAK1-9 plasmid DNA (lanes 1 and 2), and pcDIAPK1 (lanes 3 and 4) were used in a TNT coupled reticulocyte lysate system in the presence (+) or absence (−) of pancreatic microsomal membrane (m). The products were resolved on a 10% reducing SDS-PAGE and autoradiographed. A 69 kD protein was produced. In the presence of pancreatic microsomes (lane 2), a slightly larger protein was observed indicating the protein had been inserted into microsomes and glycosylated. As a control, a cDNA encoding a 30 kD cytosolic protein that also reacts with MAb K1 (Chang, K., and Pastan, I., *Int. J. Cancer* 57, 90-97 (1994)) was subjected to the same analysis. The size of the protein was unaffected by the presence of microsomes.

2. Expression in cultured cells. pcDICAK1-9 was transfected into COS cells for transient expression. pcDNAI/Amp vectors with insert 9 or without insert were transfected into COS cells. Two days later, the cells were immunocytochemically labeled with MAb K1 at 4° C. (for surface labeling) or at 23° C. (for intracellular labeling) and photographed (Magnification ×250). The specific labeling pattern of COS cells transfected with insert 9 using MAb K1 was observed. In nonpermeabilized cells, a typical cell surface fluorescent pattern is detected. In permeabilized cells, strong staining of the Golgi region is evident. No cytosolic staining was detected. Also, no immunoreactivity was detected in cells transfected with vector without insert or control inserts. Thus, insert 9 encodes a cell surface protein that is also present in the Golgi.

3. Size and processing of CAK1 antigen. To determine the size of the antigen produced by cells transfected with insert 9, NIH 3T3 cells were transfected with pcD3CAK1-9 to make stable cell lines. Stably transfected clones were produced as described above and the presence of antigen on the surface was confirmed by immunofluorescence. Then membrane and cytosolic fractions were prepared from NIH 3T3 K20 cells and from OVCAR-3 cells, subjected to SDS-PAGE and analyzed by immunoblotting with MAb K1. Approximately 100 μg of membrane fraction (lanes 1 and 3) or cytosolic fraction (lanes 2 and 4) of the transfected NIH 3T3 (pcD3CAK1) and mock control (pcD3) and membrane (lane 5) or cytosolic fraction (lane 6) of OVCAR-3 cells were electrophoresed and immunoblotted with MAb K1. As previously reported, the major reactivity in OVCAR-3 cells is with a doublet of about 40 and 43 kD that is present in membranes but not in the cytosol. In the transfectants, two bands of equal intensity were detected in the membrane fraction; one of about 40 kD and a second of about 71 kD. No signal was detected in the cytosol. These data suggest that CAK1 is made as a large molecular weight precursor that is processed by proteolysis to an approximately 40 kD form.

4. Nature of cell surface attachment. To determine if CAK1 was attached to the transfectants via a PI linkage as it is in OVCAR-3 cells (Chang, K., et al., *Cancer Res.* 52, 181-186 (1992)), the NIH 3T3 transfectant cell line k20 was treated with PI-PLC for 60 min. The transfected NIH 3T3 k20 cells were treated with PI-PLC and labeled with MAb K1 as described above. The CAK1 signal was completely abolished after PI-PLC treatment. A strong cell surface labeling pattern was observed in untreated cells. Fluorescence was absent after treatment with PI-PLC. In phase contrast images before (B) and after (D) treatment, the treated cells are still attached to the dish but are slightly altered in shape. The medium from PI-PLC treated cells was concentrated, subjected to SDS-PAGE and analyzed with MAb K1. A band of about 70kD was detected, but no lower molecular weight bands were detected.

C. Summary of Results

Thus, the above describes the molecular cloning of the CAK1 antigen which is found on mesothelium, mesotheliomas, ovarian cancers and some squamous cell carcinomas. We have designated this antigen mesothelin to reflect its presence on mesothelial cells. One unexpected feature of mesothelin is that its cDNA encodes a 69 kD protein, whereas the antigen present on OVCAR-3 cells, used to isolate MAb K1, has a molecular weight of 40,000 Daltons. The DNA sequence and the deduced amino acid sequence of CAK1 is shown in FIG. 1. The cDNA is 2138 bp in length and contains an open reading frame of 1884 bp. The protein it encodes contains 628 amino acids with a calculated molecular weight of 69001 daltons. A homology analysis was performed with nucleotide or amino acid sequences and none was detected using EMBL-GenBank accessed by the GCG program. The protein contains four potential N-linked glycosylation sites N-X-S or N-X-T that are shown in bold letters. A typical signal sequence is not present at the amino terminus. However, a short hydrophobic segment is located 15 amino acids from the first methionine (FIG. 1). This sequence might function as a signal sequence for membrane insertion, because the protein is found on the cell surface and is inserted into microsomes during cell free translation. Also present is a putative proteolytic processing site, RPRFRR (SEQ ID NO:8), beginning at amino acid 293 (FIG. 1). This site is recognized by furin, a protease important in the processing of several membrane proteins as well as in the activation of *Pseudomonas* and diphtheria toxins (Chiron, M. F., et al., *J.B.C.* 269(27):18169-18176 (1994)). The 40 kD form appears to be derived from a 69 kD precursor by several processing steps. These are summarized in FIG. 2. Initially, mesothelin is made as a 69 kD polypeptide with a hydrophobic tail which is probably removed and replaced by phosphatidylinositol (Chang, K., et al., *Cancer Res.* 52, 181-186 (1992)). After glycosylation at one or more of its four putative N-linked glycosylation sites, it is cleaved by a protease to yield the 40 kD fragment (or doublet) found on the surface of OVCAR-3 cells and a smaller (~31 kD) fragment. The latter could be released into the medium and/or further degraded. The amino terminal fragment has recently been detected in the medium of OVCAR-3 cells (our data). In transfected NIH 3T3 and MCF-7 cells, we find approximately equal amounts of 70 kD and 40 kD proteins. We originally detected the 40 kD form in OVCAR-3 and HeLa cells and did not notice a larger form. Reexamination of the OVCAR-3 and HeLa cell gels reveals a trace amount of the 70 kD precursor.

What is claimed is:

1. An isolated protein comprising the full-length amino acid sequence of SEQ ID NO:2.

2. A composition comprising an isolated protein comprising the full-length amino acid sequence of SEQ ID NO:2, and a pharmaceutically acceptable carrier.

3. A composition of claim 2, further comprising an adjuvant.

* * * * *